United States Patent
Lai

(10) Patent No.: US 6,382,795 B1
(45) Date of Patent: May 7, 2002

(54) METHOD AND APPARATUS FOR MEASURING REFRACTIVE ERRORS OF AN EYE

(75) Inventor: Ming Lai, Dublin, CA (US)

(73) Assignee: Carl Zeiss, Inc., Thornwood, NY (US)

( * ) Notice: Subject to any disclaimer, the term of this patent is extended or adjusted under 35 U.S.C. 154(b) by 0 days.

(21) Appl. No.: 09/576,082

(22) Filed: May 20, 2000

(51) Int. Cl.⁷ .................................................. A61B 3/10
(52) U.S. Cl. ...................................................... 351/212
(58) Field of Search ................................ 351/203, 200, 351/205, 206, 211, 212, 221, 222, 223, 236, 237

(56) References Cited

U.S. PATENT DOCUMENTS

| | | | |
|---|---|---|---|
| 4,778,268 A | * 10/1988 | Randle | 351/203 |
| 5,208,619 A | 5/1993 | Campbell | 351/211 |
| 5,455,645 A | * 10/1995 | Berger et al. | 351/223 |
| 5,777,719 A | 7/1998 | Williams et al. | 351/212 |
| 5,949,521 A | 9/1999 | Williams et al. | 351/246 |

FOREIGN PATENT DOCUMENTS

WO 27334 6/1999 ............. G01J/1/00

OTHER PUBLICATIONS

"Objective measurement of wave aberrations of the human eye with the use of a Hartmann–Shack wave–front sensor," J. Opt. Soc. Am. A, vol. 11, No. 7, pp. 1949–1957, Jul. 1994.

* cited by examiner

Primary Examiner—George Manuel
(74) Attorney, Agent, or Firm—Michael B. Einschlag

(57) ABSTRACT

Embodiments of the present invention advantageously satisfy the above-identified need in the art, and provide method and apparatus for measuring refractive errors of an eye that improve upon wavefront type refractors using a conventional Hartmann-Shack sensor. Specifically, one embodiment of the present invention is an apparatus for measuring refractive errors of an eye which includes: (a) a source of a probe beam; (b) a first Badal lens system adapted to project the probe beam into a subject's eye to form an illumination spot on a retina; (c) a second Badal lens system adapted to image the illumination spot onto an image plane substantially conjugate to the retina; and (d) a spatial filter disposed in the image plane adapted to transmit at least a portion of the image.

12 Claims, 1 Drawing Sheet

(Prior Art)

METHOD AND APPARATUS FOR MEASURING REFRACTIVE ERRORS OF AN EYE

TECHNICAL FIELD OF THE INVENTION

The present invention pertains to method and apparatus for measuring optical quality of an eye. In particular, the present invention pertains to method and apparatus for measuring refractive errors of an eye based on wavefront measurement.

BACKGROUND OF THE INVENTION

As is well known, a wavefront type refractor is an optical device for measuring refractive errors of an eye based on wavefront measurement. Such a wavefront type refractor can provide comprehensive measurement of the refractive errors of an eye, including high order refractive errors. In addition, such a wavefront type refractor may provide more accurate measurement of the refractive errors of an eye than a conventional auto-refractor. Advantageously, the wavefront measurements can be used to guide refractive laser surgery to correct detected refractive errors. In addition, such a wavefront type refractor may be used to provide prescriptions for eyeglasses and contact lenses.

One implementation of a wavefront type refractor that is well known in the art uses a "Hartmann-Shack" sensor to measure the wavefront of a light beam generated from an illumination spot projected on the retina and passed through the eye's optics. As is well known, in such a wavefront type refractor, a probe beam from a laser or a superluminescent diode is projected onto the retina through the eye's optics. Light scattered by the retina passes through the eye's optics, and emerges through the eye's pupil. The wavefront of the emerging beam carries refractive information relating to the eye's optics. For example, if the eye is emmetropic (i.e., the eye's optics is without refractive error), the wavefront of the emerging beam should be flat. Relay optics relays the wavefront emerging from eye's pupil onto the Hartmann-Shack sensor. The Hartmann-Shack sensor measures the distortion of the wavefront to determine the refractive errors of the eye due to aberrations of the eye's optics.

As is well known, a Hartmann-Shack sensor comprises a lenslet array and a CCD camera located at the focal plane of the lenslet elements of the array. Whenever a beam of radiation to be measured is projected onto a Hartmann-Shack sensor, the lenslet array breaks the beam into sub-apertures, and forms a pattern of focal spots (the pattern of the focal spots carries the signature of the wavefront of the beam to be measured). The CCD camera records the pattern of focal spots, and a computer analyzes the pattern to reconstruct the wavefront of the beam.

As one can readily appreciate from the above, the accuracy of wavefront measurement provided by the above-described wavefront type refractor depends on precise measurement of the positions of the focal spots. Good image quality of the Hartmann-Shack focal spots is thus an essential requirement of such a wavefront type refractor. To resolve the positions of the focal spots precisely, the spots need to be kept to a certain size to cover a predetermined number of pixels in the CCD camera.

One problem encountered in using a Hartmann-Shack sensor to fabricate a wavefront type refractor relates to the defocusing power of an eye. In particular, the defocusing power of an eye varies from patient to patient, and this defocusing power variation can significantly change the spot size of the probe beam on the retina. Consequently, the focal spot size on the Hartmann-Shack CCD camera can change significantly. Another problem encountered in using a Hartmann-Shack sensor to fabricate a wavefront type refractor relates to diffused scattering from a retina. In particular, diffused scattering from the retina produces a bright background for the Hartmann-Shack focal spots, and as a result, reduces image contrast. As is well known, diffused scattering form the retina is a result of the layer structure of the fibers of the retina (the layer structure serves as a two-dimensional wave-guide to enhance lateral diffusion of scattered light).

As one can readily appreciate from the above, a need exists in the art for method and apparatus for measuring refractive errors of an eye that improve upon wavefront type refractors using a conventional Hartmann-Shack sensor.

SUMMARY OF THE INVENTION

Embodiments of the present invention advantageously satisfy the above-identified need in the art, and provide method and apparatus for measuring refractive errors of an eye that improve upon wavefront type refractors using a conventional Hartmann-Shack sensor.

Specifically, one embodiment of the present invention is an apparatus for measuring refractive errors of an eye which comprises: (a) a source of a probe beam; (b) a first Badal lens system adapted to project the probe beam into a subject's eye to form an illumination spot on a retina; (c) a second Badal lens system adapted to image the illumination spot onto an image plane substantially conjugate to the retina; and (d) a spatial filter disposed in the image plane adapted to transmit at least a portion of the image. Advantageously, such an embodiment provides: (a) more accurate wavefront measurement when using a Hartmann-Shack sensor by improving a Hartmann-Shack image; (b) a probe beam spot size that is substantially independent of the defocusing power of the eye; and (c) that a minimal of diffused scattering from the retina falls onto the Hartmann-Shack image of a Hartmann-Shack sensor.

DETAILED DESCRIPTION

Figure 1:
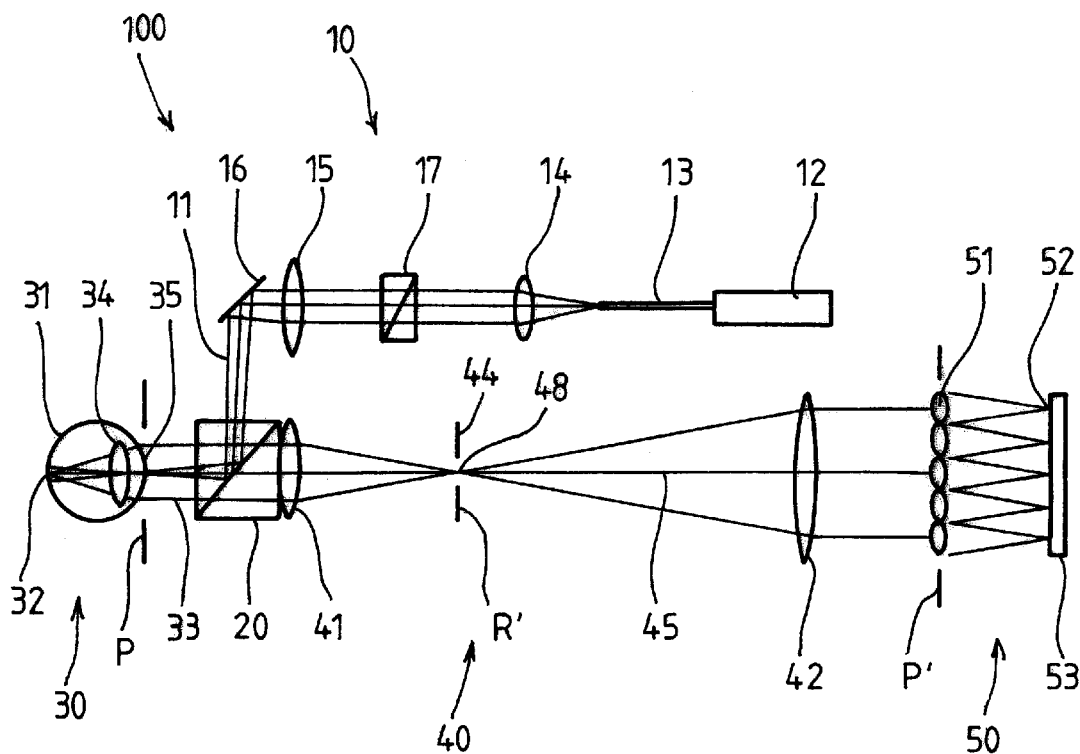
FIG. 1 shows a block diagram of a wavefront refractor that is fabricated in accordance with one embodiment of the present invention.

FIG. 1 shows a block diagram of wavefront refractor 100 that is fabricated in accordance with the present invention. As shown in FIG. 1, wavefront refractor 100 comprises probe beam assembly 10, polarizing beamsplitter 20, relay optics assembly 40, and Hartmann-Shack sensor 50.

As shown in FIG. 1, probe beam assembly 10 comprises radiation source 12 which outputs a beam of radiation, which beam of radiation is applied as input to fiber 13. The beam of radiation is typically radiation that is not detected by a patient such as, for example and without limitation, infrared or near infrared radiation. A beam of radiation output from fiber 13 passes through collimation optical system 14 (collimation lens system 14 may comprise one or more lenses) and polarizer 17 to output linearly polarized radiation (polarizer 17 can be fabricated in accordance with a number of methods that are well known to those of ordinary skill in the art). The linearly polarized beam of radiation passes through Badal lens system 15 (a Badal configuration is described in detail below), is redirected by turning mirror 16, and, as projected beam 11, impinges upon polarizing beamsplitter 20. Although only one lens is illustrated, those of ordinary skill in the art will readily understand that more than one lens is more typical of such Badal lens systems. Polarizing beamsplitter 20 directs projected beam 11 to impinge upon eye 30 to form illumination spot 32 on retina 31. Advantageously, in accordance with this embodiment of the present invention, use of Badal lens system 15, causes illumination spot 32 on retina 31 to be rendered with a spot size that is independent of the defocusing power of eye 30. As a result, the spot size of illumination spot 32 on retina 31 can be predetermined, and is substantially independent of the defocusing power of eye 30.

It is desirable to utilize a super-luminescent diode to fabricate radiation source 12 due to its high brightness and short coherence length. A desirable wavelength of the super-luminescent diode is in the near infrared spectrum range. However, other radiation sources may be used such as, for example and without limitation, a laser or a light emitting diode. In addition it is preferred that fiber 13 be a single mode fiber to enable good beam quality and fine collimation. Polarizer 17 is set to select a polarization defined by polarizing beamsplitter 20.

In accordance with this embodiment of the present invention, Badal lens system 15 is located one focal length away from pupil plane P of eye 30. As a result, probe beam 11 is focused onto pupil plane P. For an example wherein: (a) fiber 13 has a fiber core of 5 microns; (b) collimating lens 14 has a focal length of 15 mm; and (c) Badal lens system 15 has a focal length of 200 mm, the spot size on pupil plane P is about 65 microns.

In such a Badal configuration, the spot size of illumination spot 32 on retina 31 is about 300 microns for a normal eye length of 22 mm. This spot size is substantially independent of the defocusing power of eye 30, while it is proportional to eye length.

As shown in FIG. 1, light scattered from illumination spot 32 passes through the eye's optics (including eye lens 34 and cornea 35), and emerges as outgoing beam 33. The wavefront of outgoing beam 33 carries aberration information relating to the eye's optics. Polarizing beamsplitter 20 only passes a depolarized portion of outgoing beam 33 (i.e., polarizing beamsplitter 20 rejects reflections from, among other things, eye lens 34, cornea 35, and retina 31).

As shown in FIG. 1, relay optics assembly 40 comprises Badal lens system 41 and lens system 42, which Badal lens system 41 and lens system 42 may each comprise one or more lenses. Relay optics assembly 40 relays the wavefront at pupil plane P to a conjugate plane P'. As further shown in FIG. 1, Badal lens system 41 images illumination spot 32 as image spot 48 on plane R' inside relay optics assembly 40 (plane R' is a focal plane of Badal lens system 41, and is conjugated to retina 31). In accordance with this embodiment of the present invention, the spot size of the image of illumination spot 32 at plane R' is substantially independent of the defocusing power of eye 30. Further, in accordance with this embodiment of the present invention, spatial filter 44 has an aperture substantially equal to the size of the image spot, and is positioned at focal plane R' to reject trace light caused by diffused scattering on retina 31.

The position of image plane R' varies as a function of the defocusing power of eye 30. However, as is well known to those of ordinary skill in the art, the position of image plane R' can be determined using an optometer, which optometer may be used as an accessory alignment device for apparatus 100. Then, in accordance with a further embodiment of the present invention, a driving mechanism (not shown) can move spatial filter 44 to overlap image plane R'. The driving mechanism for moving spatial filter 44 may be fabricated in accordance with any one of a number of methods that are well known to those of ordinary skill in the art. For example and without limitation, spatial filter 44 may be moved by a linear motor or a motorized drive screw.

In accordance with this further embodiment of the present invention, spatial filter 44 has an aperture substantially equal to the size of image spot 48. Thus, when movable spatial filter 44 is located at image plane R', maximum transmission of outgoing beam 33 (scattered from illumination spot 32) occurs, and trace radiation from diffused scattering around illumination spot 32 is rejected. Advantageously, in accordance with this embodiment of the present invention, the use of spatial filter 44 significantly improves the contrast of an image obtained on Hartmann-Shack sensor 50, and as a result, the detection of focal spots 52 (to be described in detail below) can be more precise.

As further shown in FIG. 1, Hartmann-Shack wavefront sensor 50 comprises lenslet array 51 and CCD camera 53. Lenslet array 51 is located at plane P' and CCD camera 53 is located at the focal plane of the lenslet elements of lenslet array 51. Wavefront sensor 50 detects the wavefront of outgoing beam 33 when lenslet array 51 forms a pattern of focal spots 52 on CCD camera 53.

In accordance with this embodiment of the present invention, the output from CCD camera 53 is applied as input to an analyzer (not shown), for example, a personal computer. The analyzer then determines the x, y, z position of a centroid of focal spots in accordance with any one or a number of methods that are well known to those of ordinary skill in the art. Then, the slope of each beam segment is determined using the coordinates of the centroids to determine the slope of a portion of the beam passing through each of the elements of lenslet array 50. Next, the analyzer uses any one of a number of methods that are well known to those of ordinary skill in the art to use the slopes of the beam segments to reconstruct the wavefront of beam 33 at plane P'. For example, in one such embodiment, the analyzer fits the slopes of the beam segments to a set of Zernike polynomials to reconstruct the wavefront of beam 33 at plane P' in accordance with the teaching of an article entitled "Objective measurement of wave aberrations of the human eye with the use of a Hartmann-Shack wave-front sensor" by J. Liang et al., J. Opt. Soc. Am. A, Vol. 11, No. 7, July 1994, pp. 1949–1957 (the "Liang article"), which Liang article is incorporated by reference herein. The wavefront of beam 33 is then reconstructed at plane P via a scale factor determined by the relay optics. A comprehensive review of the Hartmann-Shack wavefront sensor, and wavefront reconstruction is found in U.S. Pat. No. 5,777,719.

Finally, the refractive errors of the eye are calculated by the analyzer in accordance with any one of a number of methods that are well known to those of ordinary skill in the art using the reconstructed wavefront. For example, one such method is disclosed in a publication of Frey et al. on Jun. 3, 1999, WO 99/27334 entitled "Objective Measurement and Correction of Optical Systems Using Wavefront Analysis" wherein distortions of the wavefront are taken as an estimate of the aberrations, which publication is incorporated by reference herein (see also the Liang article).

The use of Hartmann-Shack sensor 50 for wavefront measurement is well known in the art. However, the image quality of focal spots 52 on CCD camera 53 remains as an issue in obtaining accurate measurement of eye aberration. For example, diffused scattering from illumination spot 32 may produce a bright background on focal spots 52. Such a bright background may reduce the signal to noise ratio of focal spots 52, and thereby, make it difficult to obtain precise measurement of the position of focal spots 52. Advantageously in accordance with this embodiment of the present invention, and as described above, Badal lens system 15 provides illumination spot on retina 31 with a spot size that is independent of the defocusing power of eye 30. In addition, Badal lens system 41 provides an image spot at plane R' having a spot size that is independent of the defocusing power of eye 30. This, together with spatial filter 44, enables one to obtain a Hartmann-Shack image with reduced background from diffuse scattering. As a result, improved accuracy can be achieved for wavefront measurement.

Figure 2:
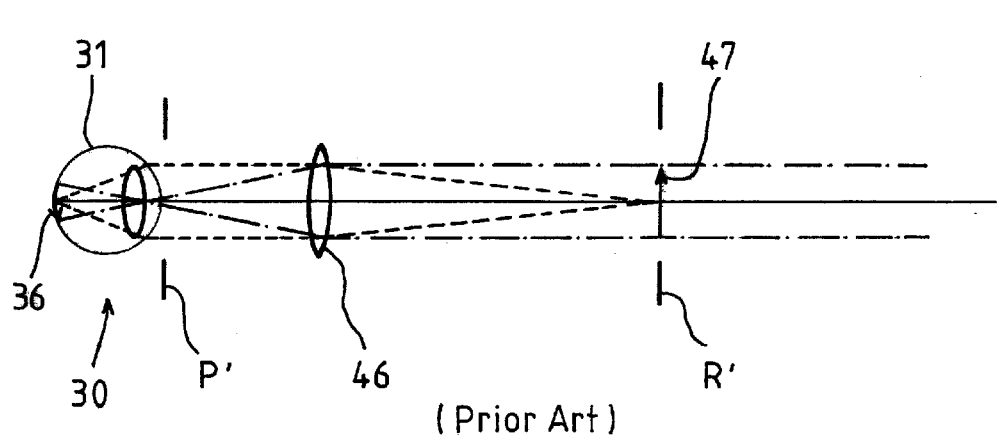
FIG. 2 shows a block diagram of a Badal optics apparatus in the prior art that is used to fabricate a preferred embodiment of the present invention.

FIG. 2 shows a block diagram of prior art Badal optics configuration 200 which produces image 36 on retina 31 having an image size that is independent of the defocusing power of eye 30. In one embodiment, Badal optics configuration 200 comprises Badal lens system 46 located one focal length away form pupil plane P of eye 30. As shown in FIG. 2, Badal lens 46 forms an image plane R' of retina 31. The distance of image plane R' from Badal lens 46 depends on the focal power of eye 30. However, target 47 located on image plane R' appears the same size, independent of the focal power of eye 30. Badal optics configurations are commonly used in optometry and a detailed description of the Badal optics configuration can be found in U.S. Pat. No. 5,208,619, which patent is incorporated by reference herein. Note that the Badal configuration shown in FIG. 1 in relay optics assembly 40 (where illumination spot 32 is imaged by Badal lens system 41 to form an image spot 48 on image plane R' conjugated to retina 31) is a reverse arrangement of an optometer (for example, as shown in FIG. 2) where target 47, located at image plane R', is imaged onto retina 31.

Those of ordinary skill in the prior art should readily appreciate that the combination of the two Badal optics configurations shown in FIG. 1 produces an image spot, image spot 48, having a spot size that is substantially independent of eye length of eye 30.

In one example of a wavefront refractor fabricated in accordance with an embodiment of the present invention, the focal length of Badal lens 41 is approximately 100 mm. This focal length is about five (5) times as long as an eye length. As a result, image spot 48 on focal plane R' is about five (5) times as large as illumination spot 32. Thus, for an illumination spot having an approximate spot size of 300 microns, spatial filter 44 should have an aperture of about 1.5 mm.

Those skilled in the art will recognize that the foregoing description has been presented for the sake of illustration and description only. As such, it is not intended to be exhaustive or to limit the invention to the precise form disclosed. For example, those of ordinary skill in the art should readily appreciate that Badal lens system 15 may be combined with collimating lens system 14 to produce a similar focal spot on pupil plane P. Further, although embodiments of the present invention has been described in conjunction with a Hartmann-Shack sensor, the present invention is not limited by this. In fact, it is within the scope and spirit of the present invention that other wavefront sensors made be used as well.

What is claimed is:

1. A wavefront refractor which comprises:

a source of a probe beam;

a first Badal lens system adapted to project the probe beam into a subject's eye to form an illumination spot on a retina;

a second Badal lens system adapted to image the illumination spot onto an image plane substantially conjugate to the retina; and a spatial filter disposed in the image plane adapted to transmit at least a portion of the image.

2. The wavefront refractor of claim 1 wherein the apparatus further comprises a driving mechanism adapted to move the spatial filter.

3. The wavefront refractor of claim 2 which further comprises a wavefront sensor disposed to receive radiation transmitted by the spatial filter.

4. The wavefront refractor of claim 3 which further comprises an analyzer, responsive to output from the wavefront sensor, to reconstruct the wavefront of the beam.

5. The wavefront refractor of claim 1 which further comprises a wavefront sensor disposed to receive radiation transmitted by the spatial filter.

6. The wavefront refractor of claim 5 which further comprises an analyzer, responsive to output from the wavefront sensor, to reconstruct the wavefront of the beam.

7. The wavefront refractor of claim 5 wherein the wavefront sensor comprises a lenslet array disposed in front of a CCD camera.

8. The wavefront refractor of claim 7 which further comprises an analyzer, responsive to output from the CCD camera, adapted to reconstruct the wavefront of the beam.

9. The wavefront refractor of claim 8 wherein the analyzer is adapted to determine a slope of beam segments associated with lenslet elements of the lenslet array, and therefrom, to reconstruct the wavefront of the beam.

10. The wavefront refractor of claim 1 wherein the first Badal lens system has a focal length of approximately 200 mm.

11. The wavefront refractor of claim 1 wherein the second Badal lens system has a focal length of approximately 100 mm.

12. The wavefront refractor of claim 1 wherein the spatial filter has an aperture of approximately 1.5 mm.

* * * * *